(12) United States Patent
Schmitt et al.

(10) Patent No.: US 6,624,301 B1
(45) Date of Patent: Sep. 23, 2003

(54) PROCESS FOR THE PREPARATION OF (CYCLO)ALIPHATIC URETDIONES OF IMPROVED COLOR QUALITY

(75) Inventors: Felix Schmitt, Herten (DE); Elmar Wolf, Recklinghausen (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 08/588,087

(22) Filed: Jan. 18, 1996

(30) Foreign Application Priority Data

Mar. 25, 1995 (DE) .......................... 195 10 956

(51) Int. Cl.$^7$ ............................................. C07D 229/00
(52) U.S. Cl. ....................................................... 540/202
(58) Field of Search .......................................... 540/202

(56) References Cited

U.S. PATENT DOCUMENTS

| | | | | |
|---|---|---|---|---|
| 2,671,082 A | * | 3/1954 | Stallmann | 260/239 |
| 3,993,641 A | * | 11/1976 | Tiemann et al. | 260/239 A |
| 4,614,785 A | * | 9/1986 | Richter et al. | 528/45 |
| 4,825,003 A | * | 4/1989 | Ono et al. | 568/490 |
| 4,912,210 A | * | 3/1990 | Disteldorf et al. | 540/202 |
| 4,994,541 A | * | 2/1991 | Dell et al. | 528/51 |
| 5,237,058 A | * | 8/1993 | Laas et al. | 540/202 |

\* cited by examiner

*Primary Examiner*—Deepak Rao
(74) *Attorney, Agent, or Firm*—Oblon, Spivak, McClelland, Maier & Neustadt, P.C.

(57) ABSTRACT

Process for the preparation of (cyclo)aliphatic uretdiones of improved color quality by reaction of (cyclo)aliphatic diisocyanates, if desired in an inert solvent, with the aid of from 0.5 to 3% by weight of a catalyst of formula (I)

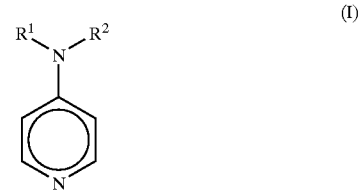

(I)

in the presence of from 0.1 to 4% by weight of a phosphorus compound of formula (II)

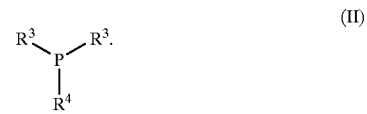

(II)

15 Claims, No Drawings

PROCESS FOR THE PREPARATION OF (CYCLO)ALIPHATIC URETDIONES OF IMPROVED COLOR QUALITY

BACKGROUND OF THE INVENTION

1. Field of the Invention

The present invention relates to a process for the preparation of (cyclo)aliphatic uretdiones having improved color quality.

2. Discussion of the Background

The preparation of (cyclo)aliphatic uretdiones is described in DE-A 37 39 549. They can be processed to give lightfast PUR powders. A disadvantage of the (cyclo) aliphatic uretdiones of DE-A 37 39 549 is their more or less severe discoloration. Surprisingly, it has been possible to largely eliminate such discoloration if a trivalent, phosphorus compound is present during the dimerization of the diisocyanate.

SUMMARY OF THE INVENTION

An object of the invention is to provide a process for the preparation of (cyclo)aliphatic uretdiones of improved color quality by reaction of (cyclo)aliphatic diisocyanates, if desired in an inert solvent, with the aid of from 0.5 to 3% by weight of a catalyst of formula (I)

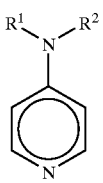

(I)

in the presence of from 0.1 to 4% by weight of a phosphorus compound of formula (II)

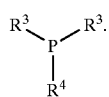

(II)

DETAILED DESCRIPTION OF THE PREFERRED EMBODIMENTS

The invention provides a process for the preparation of (cyclo)aliphatic uretdiones of improved color quality by dimerization reaction of (cyclo)aliphatic diisocyanates, if desired in an inert solvent, with the aid of from 0.5 to 3% by weight of a catalyst of formula (I)

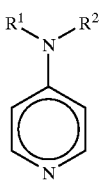

(I)

in which $R^1$ and $R^2$ are identical or different alkyl radicals of 1 to 8 carbon atoms or, together with the nitrogen atom to which they are attached, form a 5-membered or 6-membered ring which can contain a CH—$CH_3$ group, a N—$CH_3$ group or an oxygen atom in place of one $CH_2$ group in the ring, in the presence of from 0.1 to 4% by weight of a phosphorus compound of formula (II)

(II)

in which $R^3$ and $R^4$ are identical or different aromatic or araliphatic hydrocarbon radicals of 1 to 10 carbon atoms or are $OR^1$ or OH. The dimerization is first carried out at temperatures of from 0 to 60° C. up to a conversion of from 5 to 70% and then the 1,3-diazacyclobutane-2,4-dione formed is isolated as a residue, without prior deactivation of the catalyst, from the reaction mixture by thin-film distillation. The amine catalyst, phosphorus compound and unreacted diisocyanate are isolated from the reaction mixture by thin-film distillation as the distillate. German patent application 195 10 956.2 filed Mar. 25, 1995 is incorporated herein by reference in its entirety.

The catalysts are employed in quantities of from 0.5 to 3% by weight, preferably from 1 to 2% by weight. They are N,N-disubstituted 4-aminopyridine derivatives, such as 4-dimethylaminopyridine, 4-diethylaminopyridine, 4-pyrrolidinopyridine, 4-piperidinopyridine and 4-(4-methylpiperidino)pyridine.

The phosphorus compounds are trivalent phosphorus compounds such as, for example, triphenylphosphine, triethyl phosphite, tributylphosphite, dibutylphosphite and dibenzylphosphite. They are added in quantities of from 0.1 to 4% by weight, preferably from 0.5 to 2% by weight, to the diisocyanate to be dimerized. The (cyclo)aliphatic diisocyanates employed according to the process of the invention contain from 6 to 15 carbon atoms.

The process according to the invention is conducted such that, first of all, dimerization is carried out with the aid of an amino catalyst and a phosphorus compound described above, up to a conversion degree which still permits conveying the reaction mixture in the liquid state at room temperature. This ranges generally from 20 to 60% diisocyanate conversion, preferably 30 to 50%. Then the unreacted diisocyanate together with the catalyst and the phosphorus compound are separated from the reaction product by thin-film distillation. The diisocyanate distilled off (plus catalyst and phosphorus compound) can be recycled to the reaction.

The reaction temperature is within a range from 0 to 60° C., preferably from 10 to 30° C. At higher temperatures, the catalytic conversion of the uretdione to the corresponding isocyanurate is clearly-evident.

The reaction time—the time within which, for example, from 40 to 60% of the diisocyanate has reacted—depends (at constant temperature) to a great extent on the concentration and on the nature of the catalyst employed. It is generally from 10 to 90 hours. The reaction can be carried out in polar solvents, such as esters, ethers and ketones, or without solvent. It is preferably carried out without solvent.

The reaction mixture is worked up by thin-film distillation at from 100 to 180° C. and from 0.01 to 0.5 mbar.

The uretdiones prepared by the process according to the invention are distinguished from the uretdiones of DE-A 37 39 549 by improved color quality.

Examples 1 to 12

The uretdiones of isophorone diisocyanate (IPDI) listed in the table below were prepared by reacting, in a first stage, IPDI with the catalyst and with the phosphorus compound at 25° C. under $N_2$ blanketing up to a conversion of from 30 to 40% and, in a second step, separating off the unreacted IPDI together with the catalyst and phosphorus compound, by thin-film distillation at140° C./0.1 mbar, from the reaction product, which contained only slight traces of catalyst (0.05%) and phosphorus compound (<0.1%).

TABLE 1

Catalytic dimerization of IPDI in the presence of triphenylphosphine

| Example | 1 | 2 | 3 | 4 | 5 | 6 | 7 | 8 |
|---|---|---|---|---|---|---|---|---|
| IPDI | ←--------------------------------------------------------------------→ | | | | | | | |
| DMAP*) % by wt. | 1 | 2 | 1 | 2 | — | — | — | — |
| 4-Pyrrolidinopyridine % by wt. | — | — | — | — | 1 | 2 | 1 | 2 |
| Triphenylphosphine % by wt. | — | — | 1 | 1 | — | — | 1 | 1 |
| Reaction time hours | 72 | 25 | 72 | 25 | 41 | 18 | 41 | 18 |
| % NCO | 29.7 | 30.0 | 29.2 | 29.6 | 29.5 | 29.0 | 28.9 | 28.9 |
| $n_D^{25}$ | 1.4932 | 1.4925 | 1.4942 | 1.4940 | 1.4929 | 1.4940 | 1.4948 | 1.4956 |
| Color (Hazen) | 267 | 389 | 114 | 112 | 303 | 361 | 130 | 183 |
| | ↓ Thin-film distillation 140° C./0.1 mbar | | | | | | | |
| % NCO | 17.6 | 17.9 | 17.8 | 17.8 | 17.5 | 17.6 | 17.4 | 17.8 |
| % IPDI | 0.6 | 0.7 | 0.6 | 0.3 | 0.3 | 0.5 | 0.3 | 0.3 |
| Color number (Hazen) (70% strength in butyl acetate) | 248 | 227 | 147 | 219 | 308 | 401 | 250 | 223 |

*)4-Dimethylaminopyridine

TABLE 2

Catalytic dimerization of IPDI in the presence of tributyl phosphite

| Example | | 9 | 10 | 11 | 12 |
|---|---|---|---|---|---|
| IPDI | | ←----------------------------→ | | | |
| DMAP | % by wt. | 1 | 2 | — | — |
| 4-Pyrrolidino-pyridine | % by wt. | — | — | 1 | 2 |
| Tributyl phosphite | % by wt. | 1 | 2 | 1 | 1 |
| Reaction time | hours | 72 | 25 | 41 | 18 |
| % NCO | | 29.6 | 29.9 | 29.2 | 29.0 |
| $n_D^{25}$ | | 1.4933 | 1.4924 | 1.4942 | 1.4948 |
| Color (Hazen) | | 94 | 97 | 112 | 136 |
| | | ↓ Thin-film distillation 140° C./0.1 mbar | | | |
| % NCO | | 17.6 | 17.7 | 17.8 | 17.8 |
| % IPDI | | 0.4 | 0.3 | 0.4 | 0.5 |
| Color number (Hazen) (70% strength in butyl acetate) | | 102 | 106 | 118 | 125 |

Obviously, numerous modifications and variations of the present invention are possible in light of the above teachings. It is therefore to be understood that within the scope of the appended claims, the invention may be practiced otherwise than as specifically described herein.

What is claimed is:

1. Process for the preparation of (cyclo)aliphatic uretdiones consisting essentially of:

contacting a (cyclo)aliphatic diisocyanate and from 0.5 to 3% by weight of a catalyst of formula (I)

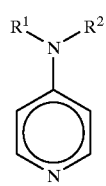

(I)

in which $R^1$ and $R^2$ are identical or different alkyl radicals of 1 to 8 carbon atoms or, together with the nitrogen atom to which they are attached, form a 5-membered or 6-membered ring which can contain a $CH\text{-}CH_3$ group, a $N\text{-}CH_3$ group or an oxygen atom in said ring, in the presence of from 0.1 to 4% by weight of a phosphorus compound of formula (II)

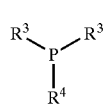

(II)

in which $R^3$ and $R^4$ are identical or different aromatic or araliphatic hydrocarbon radicals of 1 to 10 carbon atoms or are $OR^1$ or OH, to effect dimerization, said contacting first being carried out at a temperature from 0 to 60° C. up to 5 to 70% conversion and then isolating a residue containing 1,3-diazacyclobutane-2,4-dione from the reaction mixture by thin-film distillation, without prior deactivation of the catalyst and the phosphorus compound, and isolating a distillate containing the catalyst, phosphorus compound and unreacted diisocyanate.

2. The process according to claim 1, wherein the reaction is carried out at a temperature of from 10 to 30° C.

3. The process of claim 1, wherein said catalyst is employed in quantities of from 1 to 2% by weight.

4. The process of claim 1, wherein the phosphorus compound is employed in quantities of from 0.5 to 2% by weight.

5. The process of claim 1, herein thin-film distillation is begun after a conversion of from 20 to 50%.

6. The process of claim 1 wherein the catalyst is selected from the group consisting of 4-dimethylaminopyridine, 4-diethylaminopyridine, 4-pyrrolidinopyridine, 4-piperidinopyridine and 4-(4-methylpiperidino)pyridine.

7. The process of claim 1, wherein the phosphorus compound is selected from the group consisting of triphenylphosphine, triethylphosphite, tributylphosphite, dibutylphosphite and dibenzylphosphite.

8. The process of claim 1, wherein the reaction is carried out without solvent.

9. The process of claim 1, wherein isophorone diisocyanate is employed as said diisocyanate.

10. The process of claim 1, wherein the phosphorus compound is selected from the group consisting of triethylphosphite, tributylphosphite, dibutylphosphite and dibenzylphosphite.

11. The process of claim 10, wherein the phosphorus compound is tributylphosphite.

12. The process of claim 11, wherein the catalyst is 4-pyrrolidinopyridine.

13. The process of claim 10, wherein isophorone diisocyanate is employed as said diisocyanate.

14. The process of claim 11, wherein isophorone diisocyanate is employed as said diisocyanate.

15. The process of claim 12, wherein isophorone diisocyanate is employed as said diisocyanate.

* * * * *